(12) United States Patent
Schneider (10) Patent No.: US 7,160,913 B2
(45) Date of Patent: Jan. 9, 2007

(54) METHODS AND KIT FOR TREATING PARKINSON'S DISEASE

(75) Inventor: Jay S. Schneider, Cherry Hill, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 300 days.

(21) Appl. No.: 10/660,090

(22) Filed: Sep. 11, 2003

(65) Prior Publication Data

US 2004/0087596 A1    May 6, 2004

Related U.S. Application Data

(60) Provisional application No. 60/410,512, filed on Sep. 13, 2002.

(51) Int. Cl.
*A61K 31/196* (2006.01)
*A61K 31/42* (2006.01)

(52) U.S. Cl. .................................. 514/380; 514/561

(58) Field of Classification Search ................ None
See application file for complete search history.

(56) References Cited

U.S. PATENT DOCUMENTS

| | | | | |
|---|---|---|---|---|
| 4,904,681 | A | 2/1990 | Cordi et al. | 514/380 |
| 5,260,324 | A | 11/1993 | Cordi et al. | 514/376 |
| 5,668,117 | A | 9/1997 | Shapiro | 514/55 |
| 6,284,776 | B1 | 9/2001 | Meltzer | 514/326 |
| 6,294,583 | B1 | 9/2001 | Fogel | 514/665 |
| 6,417,210 | B1 | 7/2002 | Melamed et al. | 514/367 |
| 6,551,993 | B1* | 4/2003 | Schneider | 514/8 |

| | | | | |
|---|---|---|---|---|
| 2002/0035145 | A1 | 3/2002 | Tsai et al. | 514/472 |

FOREIGN PATENT DOCUMENTS

| WO | WO 97/39797 | 4/1997 |
|---|---|---|
| WO | WO 99/52519 | 4/1999 |
| WO | WO 01/12190 | 2/2001 |

OTHER PUBLICATIONS

Laake K. Oeksengaard AR, (2002) "D-cycloserine for Alzheimer's disease," *The Cochrane Library*, Issue 4.
Wadie Najm, M.D. (2002), "Using Complementary Treatments in Dementia," *Center for clinical Age Management, Inc.*
Sophie Erhardt, (2001), "Importance of endogenous kynurenic acid in brain catecholaminergic processes and in the pathophysiology of schizophrenia," *Doctor's Thesis from Karolinska Institutet* 91:628-4889-5.
V. Lelong et al., (2001), "RS 67333 and D-cycloserine accelerate learning acquisition in the Rat.," *Neuropharmacology* 41:517-522. (abstract only).
B.N.M. van Berckel et al., (1998), "original investigation: The partial NMDA agonist D-cycloserine stimulates LH secretion in healthy volunteers," *Psychopharmacology-Abstract*, 138:190-197. (abstract only).
P. Riekkinen Jr. et al., (1998), "D-cycloserine, a partial NMDA receptor-associated glycine-B site agonist, enchances reversal learning, but a cholinesterase inhibitor and nicotine has no effect," *NeuroReport*, 9:3647-3651. (abstract only).

(Continued)

*Primary Examiner*—Phyllis G. Spivack
(74) *Attorney, Agent, or Firm*—Drinker Biddle & Reath LLP (57) ABSTRACT

The efficacy of levodopa therapy in patients being treated for Parkinson's disease is enhanced by administering high doses of a partial glycine agonist. The frequency and severity of levodopa-induced side effects in Parkinson's disease patients are also reduced by administration of a partial glycine agonist.

15 Claims, 4 Drawing Sheets

Exhibit A

OTHER PUBLICATIONS

J.F. Disterhoft et al., (1997), "Mechanisms of associative learning in young and aging hippocampus," *Journal of Physiology*, 501:6S.

Robert van Reekum, MD FRCPC et al., (1997), "Cognition-Enhancing Drugs in Dementia: A Guide to the Near Future," *Can J Psychiatry*, 42:35S-50S.

J.W. Allen, B.S., (1996), "A Review of the Actions of D-cycloserine, a Putative Nootropic Agent, at the NMDA Receptor Complex-Associated Glycine Binding Site," *MJM*, 2:40-50.

R.B. Rosse et al., (1996), "D-cycloserine adjuvant therapy to molindone in the treatment of schizophrenia," *Clin Neuropharmacol*, 19:444-450. (abstract only).

M. Pitkanen et al., (1995), "The effects of d-cycloserine, a partial agonist at the glycine binding site, on spatial learning and working memory in scopolamine-treated rats," *J Neural Transm Park Dis Dement*, 9:133-144. (abstract only).

"Treatment of Negative Symptoms in Schizophrenia," *Fiscal Year 2000 NIH GPRA Research Program Outcomes*, p. 465. (abstract only).

("Psychosis in Late Life, Ongoing Research," *Geriatric Consultant Resources LLC*, accessed from: http://www.gcrweb.com/PsychosisDSS/clinical/pyalt.html on Jan. 16, 2003.

Donald Goff, M.D., "Glycine and D-Cycloserine in Schizophrenia," *NIMH Study ID No. MH57708* study started 1998/completed 2002; record accessed on Jan. 16, 2003 from http://www.clinicaltrials.gov/show/NCT00000372 (abstract only).

\* cited by examiner

Exhibit A

METHODS AND KIT FOR TREATING PARKINSON'S DISEASE

CROSS-REFERENCE TO RELATED APPLICATIONS

This application claims the benefit of co-pending U.S. provisional application Ser. No. 60/410,512, filed on Sep. 13, 2002, the entire disclosure of which is herein incorporated by reference.

FIELD OF THE INVENTION

The invention relates to therapies for Parkinson's Disease ("PD"), and in particular to methods and a kit for enhancing the efficacy of levodopa treatment and reducing levodopa-induced side effects with high doses of a partial glycine agonist.

BACKGROUND of the INVENTION

Parkinson's disease is a progressive disorder of the central nervous system affecting over 1.5 million people in the United States. Parkinson's disease is caused by the degeneration of the pigmented neurons in the substantia nigra of the brain, resulting in decreased dopamine availability to the striatum. Clinically, the disease is characterized by a decrease in spontaneous movements, gait difficulty, postural instability, rigidity and tremor.

The most common and effective drug for treatment of PD is levodopa, either administered alone or in combination with a peripheral dopa decarboxylase inhibitor such as carbidopa. After about 5 years of treatment, however, the majority of PD patients experience a "wearing-off" of drug effect, and often exhibit abnormal motor side effects (e.g., dyskinesias and dystonias) in response to the levodopa. These problems limit the long-term benefit that can be achieved with this drug.

Currently, the dose of levodopa can be reduced somewhat by adding dopamine agonists such as bromocriptine mesylate (Parlodel), pergolide mesylate (Permax), pramipexole (Mirapex), or ropinirole hydrochloride (Requip), however, these drugs have no effect on the duration of anti-parkinson efficacy of levodopa. Enzyme inhibitors such as a catechol-O-methyl transferase inhibitors (tolcapone or entacapone) or monoamine oxidase B inhibitors (selegiline) may extend the duration of levodopa's therapeutic effect. However, dopamine agonists and enzyme inhibitors directly manipulate dopamine neurochemistry. Side effects related to excess dopaminergic neurotransmission, such as dyskinesias and psychoses, are thus often produced when these drugs are used in conjunction with levodopa to treat PD. Also, neither the dopamine agonists nor the enzyme inhibitors have significant anti-Parkinson effects of their own.

Up to 80% of PD patients on levodopa therapy develop levodopa-induced, choreiform dyskinesias after 2–5 years of levodopa use. When levodopa-induced dyskinesias first emerge, they are mainly the peak-dose type; i.e., the dyskinesias are most prominent in PD patients when plasma levodopa levels are high. After chronic levodopa treatment, dyskinesias can appear at the beginning and again at the end of the period during which an individual levodopa has a beneficial effect. In more advanced PD, dyskinesias can be present throughout the duration of a single oral dose of levodopa, often masking any beneficial effects of the drug.

Functional models of levodopa-induced dyskinesias suggest that there is enhanced excitation in the striatum, which may be linked to the spontaneous release of glutamate after dopamine denervation. Drugs that act directly to antagonize glutamate receptors would likely not be useful in treating levodopa-induced dyskinesias, since there is little evidence of gross alterations in the levels or synthesis of any glutamate receptor subtype in parkinsonian brains. Thus, the abnormal glutamate-mediated influences that underlie levodopa-induced dyskinesias are most likely caused by altered glutamate neurotransmission.

Drugs such as amantadine or riluzole have recently been proposed as anti-dyskinesia treatments to be used in conjunction with levodopa. Some of these drugs reduce the efficacy of levodopa while minimizing dyskinesias, but none have enhanced the therapeutic effect of levodopa. Moreover, amantadine as well as other drugs that indiscriminately block glutamate receptors can cause confusion, hallucinations, depression, nightmares, and blurred vision, and the anti-dyskinetic effect wears off after a few weeks of treatment.

Chronic levodopa therapy can also cause other sides effects such as dystonias (e.g., sustained muscle contractions resulting in abnormal postures). The type and pattern of levodopa side effects can differ from patient to patient. It is not known why levodopa causes different side effects in different patients; however, dystonias and dyskinesias are believed to be caused by dysfunctions in different neural systems.

The emergence of levodopa-induced side effects presents a dilemma for the management of PD patients. For example, a decrease in the levodopa dose may relieve the side effects, but is achieved at the expense of increasing PD symptoms. In pharmacological terms, the therapeutic index of levodopa lessens over time, because the incidence of toxic side-effects increases for a given levodopa dose over the course of treatment.

Altered N-methyl D-aspartate ("NMDA") receptor transmission may also be involved in abnormal neural activity in basal ganglia circuits following dopamine depletion in PD patients. Receptor binding studies have shown that NMDA receptors in dopamine-depleted striata have increased neuron "activatability" in the presence of glutamate and glycine. Also, the animal experimental literature reports that antagonists of excitatory NMDA receptors may exert anti-parkinsonian effects.

However, the clinical usefulness of specific NMDA antagonists in treating PD is limited, because such drugs produce severe, debilitating side effects. Likewise, although drugs that block specific NMDA receptor subtypes may have some anti-parkinson properties and may reduce dyskinesias, it is unclear which NMDA subtypes need to be blocked to effectively treat PD.

Drugs that can simultaneously act as both agonists and antagonists and are called "partial agonists." The agonist or antagonist properties of such drugs are often dependent on their concentration within the brain relative to endogenous neurotransmitter levels. In parts of the brain where endogenous neurotransmitter levels are relatively low, a partial agonist can increase receptor stimulation. In regions where neurotransmitter levels are relatively high, partial agonists can act as antagonists and reduce receptor stimulation.

Glycine is a coagonist of the NMDA receptor with respect to activation of both the glutamate and glycine sites required for channel opening. Drugs like D-cycloserine or 1-aminocyclopropanecarboxylic acid (ACPC) are partial agonists for the glycine binding site of the NMDA receptor. These drugs, also called "partial glycine agonists," can act as agonists or antagonists at the NMDA receptor glycine binding site, depending on their concentration in the brain relative to endogenous glycine. Generally, partial glycine agonists act as antagonists at high concentrations in the brain relative to glycine, without directly blocking the NMDA receptor.

The partial glycine agonists have no affinity for neurotransmitter uptake sites, and, unlike NMDA channel blockers, do not produce motor incoordination or ataxia. Thus, partial glycine agonists acting as antagonists have a safer side effect profile compared to drugs that act directly on NMDA, adrenergic, histaminergic, cholinergic or glutamatergic receptors.

There is a need for a drug which increases the therapeutic efficacy of levodopa in PD patients without producing toxic side-effects related to excess dopamine neurotransmission, or the direct inhibition of NMDA and other neuroreceptors. Ideally, the treatment would also reduce the severity and frequency of levodopa-induced dyskinesias in PD patients during the course of levodopa therapy.

SUMMARY OF THE INVENTION

It has now been found that the therapeutic efficacy of levodopa in treating PD is improved when administered with high doses of a partial glycine agonist. The frequency and severity of levodopa-induced motor side-effects, such as dyskinesias and dystonias, are also reduced when levodopa is administered with a high dose of a partial glycine agonist.

The invention therefore provides a method for treating Parkinson's disease in a subject in need of such treatment, comprising administering levodopa and a high dose of a partial glycine agonist to the subject, wherein the efficacy of the levodopa is enhanced or the frequency and severity of levodopa-induced side effects in the subject is reduced.

The invention also provides a method for increasing the therapeutic index of levodopa in a subject being treated for Parkinson's disease, comprising administering levodopa and a high dose of a partial glycine agonist to the subject.

The invention also provides a method of treating PD in a subject in need of such treatment, comprising administering a high dose of a partial glycine agonist to the subject.

The invention further provides kit comprising a partial glycine agonist and instructions for administering the partial glycine agonist at a high dose, either alone or in combination with levodopa, for the treatment of Parkinson's disease.

DETAILED DESCRIPTION OF THE INVENTION

It has now been found that administering a high dose of a partial glycine agonist to subjects undergoing levodopa therapy and levodopa enhances the duration of effect of levodopa (i.e., prevents the "wearing off" phenomenon), provides a greater therapeutic effect than levodopa alone, and decreases the severity and frequency of side effects that result from long-term use of levodopa. Treatment of PD patients with a high dose of a partial glycine agonist and levodopa also allows for a decrease in levodopa dosage, which helps delay the wearing-off effect and the onset of levodopa-induced side effects.

Partial glycine agonists acting as antagonists also decrease neuronal excitotoxicity caused by excessive glutamate neurotransmission in the parkinsonian brain. Decreasing neuronal excitotoxicity has antidepressant and anxiolytic effects, and can also have a positive effect on certain types of cognitive disorders. Depression and anxiety are common complications in subjects with PD. Thus, treatment of these complications is an added advantage to the administration of a partial glycine agonist with levodopa.

A subject suffering from PD can therefore be treated with levodopa and a high dose of a partial glycine agonist. Partial glycine agonists are known to those skilled in the art, and include D-cycloserine, and 1-aminocyclopropanecarboxylic acid (ACPC). As used herein, a partial glycine agonist also includes substances which convert other substances into a partial glycine agonist in the body. A preferred partial glycine agonist is D-cycloserine.

As used herein, a "high dose" of a partial glycine agonist is a dose which produces a partial glycine agonist concentration in the brain of a subject at which the partial glycine agonist antagonizes the glycine binding site of the NMDA receptor. Preferably, a high dose of a partial glycine agonist is greater than 1 mg/kg body weight of the subject to be treated, for example at least 2 mg/kg, at least 3 mg/kg, at least 4 mg/kg, at least 5 mg/kg, at least 6 mg/kg, at least 7 mg/kg or at least 8 mg/kg partial glycine agonist. Preferably, at least 8 mg/kg partial glycine agonist is administered to the subject, for example 8 to 12 mg/kg partial glycine agonist.

As used herein, a "subject" is any mammal suffering from PD or exhibiting symptoms of PD. A subject can be a primate (e.g., human or macaque) or a rodent (e.g., mouse, rat or guinea pig), but is preferably a human. One skilled in the art can readily determine if a subject is suffering from PD or exhibiting PD symptoms by performing a standard clinical or neurological assessment; for example, by using the Unified Parkinson's Disease Rating Scale (UPDRS).

As used herein, "Parkinson's disease" or "PD" includes PD of any etiology, including idiopathic PD, postencephalitic PD, PD resulting from chronic manganese poisoning or carbon monoxide poisoning, parkinsonism-dementia of Guam and hemiparkisonism. PD also includes any neurological syndrome of undetermined etiology which a subject presents with neurological symptoms associated with a decrease in dopamine production or dopaminergic transmission in the brain.

The high dose partial glycine agonist can be administered to the subject by any enteral or parenteral route. Enteral administration is preferred.

Suitable enteral administration routes include oral or rectal. A preferred enteral administration route is oral. Suitable parenteral administration routes include intravascular administration (e.g. intravenous bolus injection, intravenous infusion, intra-arterial bolus injection, intra-arterial infusion and catheter instillation into the vasculature); subcutaneous injection or deposition including subcutaneous infusion (such as by osmotic pumps); intramuscular injection, intraperitoneal injection, transdermal, nasal or inhalational.

The levodopa and partial glycine agonist can be administered to a subject together or separately. For example, the levodopa and partial glycine agonist can be administered simultaneously by the same route, or can be administered by different routes or at different times. Preferably, the partial glycine agonist and levodopa are administered to the subject no more than twelve hours apart, for example no more than eight hours apart or no more than four hours apart. When the partial glycine agonist and levodopa are not administered simultaneously, the order in which the partial glycine agonist and levodopa are administered to the subject is not critical. In a particularly preferred embodiment, the partial glycine agonist and levodopa are administered to a subject at approximately the same time and by the same route.

One skilled in the art can readily determine the amount of levodopa to be administered to a subject along with high dose partial glycine agonist. In general, a subject being treated for PD receives an initial levodopa dose of 100 mg to 1 g daily, usually in 250 mg increments four times a day. The levodopa dose can be increased in increments of 100 to 750 mg/day at 3 to 7 day intervals, until a daily maintenance dose of 2.5 to 6 g/day is reached. Generally, no more than 8 g/day levodopa should be administered.

In the practice of the present method, the levodopa and partial glycine agonist can optionally be administered with a peripheral dopa decarboxylase inhibitor, such as carbidopa or benserazide. One skilled in the art can readily determine the amount of peripheral dopa decarboxylase inhibitor to be administered to a subject. In general, 10 mg of carbidopa or 15 mg of benserazide can be given 2–3 times daily with levodopa to the average adult human. Carbidopa or benserazide dosage can be adjusted upward daily until the desired effect is seen. Combined carbidopa/levodopa formulations are available commercially, for example, from Bristol Meyers Squibb Co., Princeton, N.J., as Sinemet®.

Administering a high dose of partial glycine agonist increases the efficacy of a given levodopa dose in a subject being treated for PD. As used herein, "increasing the efficacy of levodopa" refers to increasing the duration of the effect of levodopa for a given dose. The duration of effect of a levodopa dose can be measured by monitoring one or more symptoms of PD in a subject undergoing levodopa therapy with a partial glycine agonist, and comparing that to the length of time the symptoms are alleviated in a subject undergoing levodopa therapy without high dose partial glycine agonist. Alternatively, the length of time that the PD symptoms are alleviated in a subject receiving levodopa and a partial glycine agonist can be compared to the length of time that the symptoms were alleviated in same subject prior to receiving high dose partial glycine agonist.

Increasing the duration of effect of a levodopa dose with high dose partial glycine agonist allows one to give fewer levodopa doses, or to reduce the levodopa standard dose, but still achieve the same therapeutic effect. This is particularly advantageous, because giving fewer or reduced levodopa doses to a subject with PD delays the point at which levodopa becomes ineffective.

Administering a high dose of partial glycine agonist also reduces the frequency or severity of levodopa-induced side effects, such as dyskinesias and dystonias.

One skilled in the art can readily determine whether the frequency or severity of levodopa-induced dyskinesias is reduced by using any suitable technique for the clinical assessment of involuntary movements in subjects with PD. For example, the frequency and severity of levodopa-induced dyskinesias can be assessed using the Abnormal Involuntary Movement Scale (AIMS).

For example, assessment of subjects undergoing levodopa therapy with high dose partial glycine agonist are subjected to a six-week AIMS trial. During the AIMS trial, subjects fill out a detailed diary which to the severity of any dyskinesias and assess daily function according to the following scales:

Dyskinesia Intensity: 0-without dyskinesia; 1-mild dyskinesia; 2-medium dyskinesia; 3-severe dyskinesia.

Rating of Daily Function: 1-improvement of daily function as compared to the basic condition; 2-no improvement in daily function; 3-deterioration of daily function as compared to the basic condition.

A reduction in the daily AIMS scores during the course of the trial indicates that the frequency and severity of dyskinesias in being reduced. Alternatively, AIMS scores obtained after administration of levodopa and high dose partial glycine agonist to a subject can be compared to AIMS (or similar test) scores obtained for the subject prior to treatment with high dose partial glycine agonist.

One skilled in the art can also readily determine whether the frequency or severity of levodopa-induced dystonias is reduced by using any suitable technique for the clinical assessment of involuntary, sustained muscle contraction in subjects with PD. For example, frequency or severity of dystonias can be determined by clinical observation of the subject, including reflex studies, or by techniques such as electromyography (EMG) or nerve conduction velocity tests.

The invention also provides a method for increasing the therapeutic index of levodopa in a subject being treated for Parkinson's disease, comprising administering levodopa and a high dose of a partial glycine agonist to the subject.

As used herein, "therapeutic index" refers to a quantitative measure of the selectivity of a drug when a therapeutic effect ("E") and a toxic effect ("T") are being compared. The therapeutic index can then be calculated as $ED_{50}/TD_{50}$, at some arbitrary level of response observed in a subject receiving the drug. The $ED_{50}$ is the dose required to generate the desired intensity of therapeutic effect in 50% of the subjects tested. The $TD_{50}$ is the dose required to generate the toxic effect in 50% of the subjects tested.

The therapeutic index is a useful indicator of the benefit versus adverse effect of a drug. Those drugs which have a high therapeutic index can be administered over a wide range of effective doses without incurring significant adverse events. Conversely, drugs having a small therapeutic index can be administered over a small range of effective doses without incurring significant adverse events. The therapeutic index of levodopa lessens over time with chronic administration.

As discussed above, high doses of partial glycine agonist increase the efficacy of levodopa while also reducing toxic side effects. Thus, the therapeutic index of levodopa is increased by administration of a high dose partial glycine agonist. As discussed above, techniques for determining whether the efficacy of levodopa has increased, and whether toxic side effects of levodopa have been reduced, are within the skill in the art. Suitable doses of the partial glycine agonist and suitable routes of administration are as described above.

Substances which inhibit peripheral dopa decarboxylase (e.g., carbidopa or benserazide) can also be administered to subject with levodopa and a partial glycine agonist in order to increase the therapeutic index of levodopa.

In another embodiment, the invention provides a method of treating PD in a subject, comprising administering to a subject in need of such treatment a partial glycine agonist. Without wishing to be bound by any theory, it is believed that altered NMDA receptor transmission may be involved in abnormal basal ganglia activity in PD. Partial glycine agonists acting as non-selective antagonists of the NMDA receptor can correct this altered NMDA receptor transmission. Suitable doses of the partial glycine agonist and suitable routes of administration are as described above. Substances which inhibit peripheral dopa decarboxylase (e.g., carbidopa or benserazide) can also be administered to subject with levodopa and a partial glycine agonist.

The invention also provides a kit comprising a partial glycine agonist and instructions for administering a high dose of the partial glycine agonist to a subject suffering from PD. The instructions can specify that the partial glycine agonist is administered with or without levodopa. Preferably, the instructions specify that the partial glycine agonist is administered with levodopa. The instructions can also specify that the partial glycine agonist can be administered with a peripheral dopa decarboxylase inhibitor such as carbidopa or benserazide.

In one embodiment, the kit further comprises levodopa. In another embodiment, the kit further comprises levodopa and a peripheral dopa decarboxylase inhibitor. Preferably, the kit comprises a partial glycine agonist and levodopa in a single-dose pharmaceutical composition, in which the amount of partial glycine agonist is sufficient to deliver greater than 1 mg/kg body weight of the subject to be treated. For example, the single-dose pharmaceutical composition can deliver at least 2 mg/kg, at least 3 mg/kg, at least 4 mg/kg, at least 5 mg/kg, at least 6 mg/kg, at least 7 mg/kg or at least 8 mg/kg, for example 8 to 12 mg/kg, partial glycine agonist to the subject.

One skilled in the art can readily prepare pharmaceutical compositions comprising a partial glycine agonist, or comprising a partial glycine agonist and levodopa, for example by using the principles set forth in *Remington's Pharmaceutical Science*, $18^{th}$ edit. (Alphonso Gennaro, ed.), Mack Publishing Co., Easton, Pa., 1990. Preferred pharmaceutical compositions of the invention comprise a partial glycine agonist, levodopa and a peripheral dopa decarboxylase inhibitor such as carbidopa or benserazide.

In one embodiment, the invention provides a single-dose pharmaceutical composition comprising a partial glycine agonist and levodopa. As used herein, a "single-dose pharmaceutical composition" is a pharmaceutical composition in which the partial glycine agonist and levodopa are provided together in the same formulation, and in which the amount of partial glycine agonist is sufficient to deliver greater than 1 mg/kg body weight of the subject to be treated.

The pharmaceutical compositions of the invention can be in a form suitable for oral use, for example, as tablets, aqueous or oily suspensions, dispersible powders or granules, emulsions, hard or soft capsules, or syrups or elixirs. Pharmaceutical compositions of the invention intended for oral use can be prepared according to any technique suitable for the manufacture of oral pharmaceutical compositions, for example as disclosed in U.S. Pat. Nos. 4,190,672; 6,376,545; and 6,365,180, the entire disclosures of which are herein incorporated by reference.

Oral pharmaceutical compositions of the invention can contain one or more agents selected from the group consisting of sweetening agents, flavoring agents, coloring agents, and preserving agents in order to provide a pharmaceutically elegant and palatable preparation.

Pharmaceutical compositions of the invention comprising tablets can contain a partial glycine agonist, optionally with levodopa or levodopa and a peripheral dopa decarboxylase inhibitor, in admixture with non-toxic pharmaceutically acceptable excipients which are suitable for manufacture of tablets. Suitable excipients include inert diluents, for example calcium carbonate, sodium carbonate, lactose, calcium phosphate, or sodium phosphate; granulating and disintegrating agents, for example maize starch, or alginic acid; binding agents, for example starch, gelatin, or acacia; and lubricating agents, for example magnesium stearate, stearic acids, or talc. The tablets can be uncoated or they can be coated by known techniques to delay disintegration and adsorption in the gastrointestinal tract, and thereby provide a sustained action over a longer period.

Pharmaceutical compositions of the invention can also comprise hard gelatin capsules, wherein the partial glycine agonist, optionally with levodopa or levodopa and a peripheral dopa decarboxylase inhibitor, is mixed with an inert solid diluent; for example calcium carbonate, calcium phosphate, or kaolin. Pharmaceutical compositions of the invention can also comprise soft gelatin capsules, wherein the partial glycine agonist, optionally with levodopa or levodopa and a peripheral dopa decarboxylase inhibitor, is mixed with an oil medium; e.g., archis oil, liquid paraffin, or olive oil.

Pharmaceutical compositions of the invention can also comprise liquid formulations comprising a partial glycine agonist, optionally with levodopa or levodopa and a peripheral dopa decarboxylase inhibitor, in admixture with excipients suitable for the manufacture of liquid formulations. In addition to water or saline, suitable excipients for liquid formulations include suspending agents such as sodium carboxymethylcellulose, methylcellulose, hydroxypropylmethyl-cellulose, sodium alginate, polyvinylpyrrolidone, gum tragacanth, and gum acacia; dispersing or wetting agents such as lecithin, condensation products of an alkylene oxide with fatty acids (e.g., polyoxyethylene stearate), condensation products of ethylene oxide with long chain aliphatic alcohols (e.g., heptadecethyleneoxy-cetanol), condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyoxyethylene sorbitan monooleate).

Liquid formulations according to the invention can also contain one or more preservatives such as ethyl, n-propyl, or p-hydroxy benzoate; one or more coloring agents; one or more flavoring agents; or one or more sweetening agents such as sucrose, saccharin, or sodium or calcium cyclamate.

Liquid formulations according to the invention can also contain antioxidants, such as tocopherol, sodium metabisulphite, butylated hydroxytoluene (BHT), butylated hydroxyanisole (BHA), ascorbic acid or sodium ascorbate.

Liquid formulations according to the invention can also be formulated into syrups or elixirs by admixing with sweetening/thickening agents such as glycerol, sorbitol or sucrose. Syrups or elixirs can also contain a demulcent, preservative, flavoring or coloring agent.

The pharmaceutical compositions of the invention can also be in the form of a sterile, pyrogen-free preparation suitable for parenteral administration, for example as a sterile injectable aqueous suspension. This suspension can be formulated using the dispersing or wetting agents and suspending agents described above. A sterile injectable preparation according to the invention can also comprise a sterile injectable solution or suspension in a non-toxic, parenterally-acceptable diluent or solvent, for example, as a solution in 1,3-butane diol, water or saline solution. Formulation of sterile, pyrogen-free pharmaceutical compositions suitable for parenteral administration are within the skill in the art, for example as described in U.S. Pat. No. 4,190,672, supra.

The invention will now be illustrated with the following non-limiting examples.

EXAMPLE 1

Figure 1:
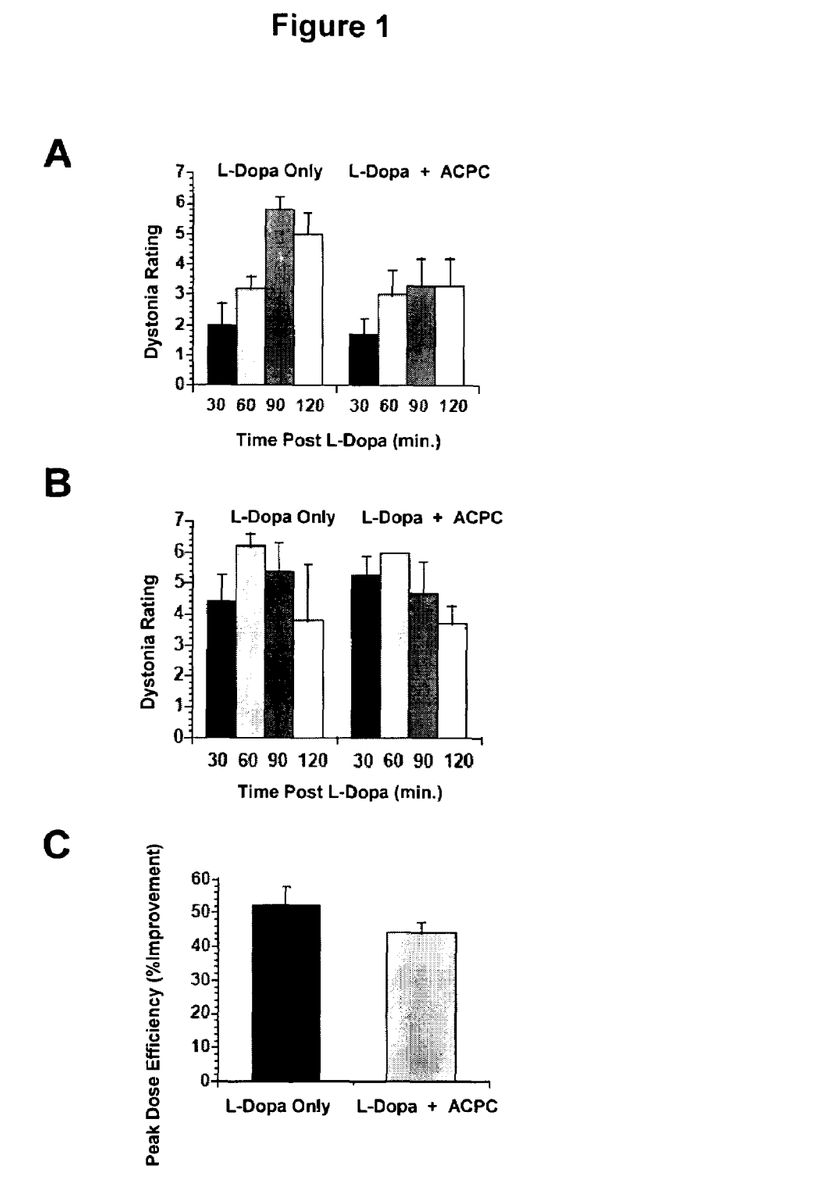
FIG. 1 is a histogram showing enhanced duration of the levodopa anti-Parkinson effect upon administration of D-cycloserine ("DCS") and levodopa/benserazide ("L-Dopa"), as compared to L-Dopa alone.

Enhanced Duration of Anti-Parkinson Effect by Combination of D-Cycloserine and Levodopa Eight mg/kg D-cycloserine was administered to two parkinsonian monkeys with an established therapeutic response to levodopa, together with 40 mg/kg levodopa plus the 15 mg of the peripheral dopa decarboxylase inhibitor benserazide. Symptomatic benefit was assessed by raters blind to treatment condition. As shown in FIG. 1, administration of partial glycine agonist with levodopa enhanced the levodopa "on" time, or duration of symptomatic relief by levodopa, by 41% compared to levodopa plus benserazide alone.

EXAMPLE 2

Figure 2:
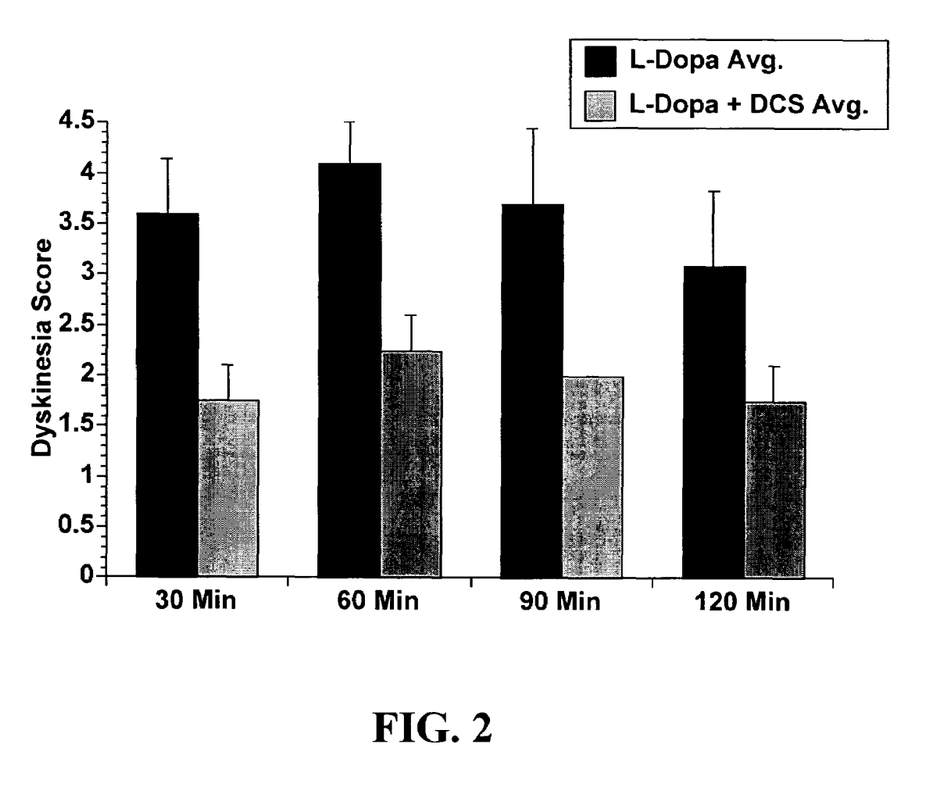
FIG. 2 is a histogram showing the inhibition of dyskinesias upon administration of D-cycloserine ("DCS") and levodopa/benserazide ("L-Dopa"), as compared to L-Dopa alone. Data are expressed as the mean (avg.) dyskinesia scores±SD.

Administration of Partial Glycine Agonist D-Cycloserine with Levodopa Reduces the Severity of Levodopa-Induced Dyskinesias A parkinsonian monkey was primed for choreiform dyskinesia following chronic administration of levodopa plus the peripheral dopa decarboxylase inhibitor benserazide. In this monkey, a 40 mg/kg challenge dose of levodopa caused significant choreiform dyskinesias (see FIG. 2; "L-Dopa Avg." bars). Eight mg/kg D-cycloserine administered with 40 mg/kg levodopa plus the 15 mg of the peripheral dopa decarboxylase inhibitor benserazide significantly decreased the severity of these dyskinesias at least over a period of 120 minutes (see FIG. 2; "L-Dopa+DCS Avg." bars). Severity of the dyskinesias was rated by observers blind to the treatment condition. Three independent repetitions of the study were performed.

EXAMPLE 3

Figure 3:
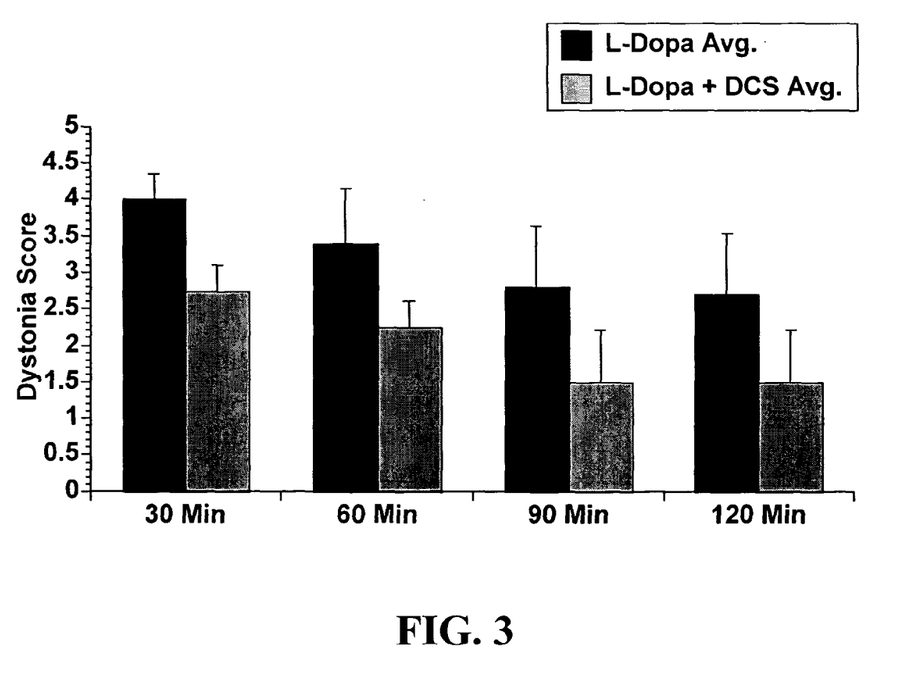
FIG. 3 is a histogram showing the inhibition of dystonia upon administration of D-cycloserine ("DCS") and levodopa/benserazide ("L-Dopa"), as compared to L-Dopa alone. Data are presented as the mean (avg.) dystonia scores±SD.

Addition of Partial Glycine Agonist D-Cycloserine to Levodopa Therapy Reduces the Severity of Levodopa-Induced Dystonias In a parkinsonian monkey, chronic administration of levodopa plus the peripheral dopa decarboxylase inhibitor benserazide resulted in primarily dystonia. Under these conditions, 8 mg/kg D-cycloserine was administered to the monkeys with 40 mg/kg levodopa plus 15 mg benserazide. The severity of the dystonia was rated by observers blind to the treatment condition. As can be seen in FIG. 3, administration of D-cycloserine ("DCS") with levodopa/benserazide ("L-Dopa") significantly decreased the severity of the dystonias at least over a period of 120 minutes. Three independent repetitions of the study were performed.

EXAMPLE 4

Figure 4:
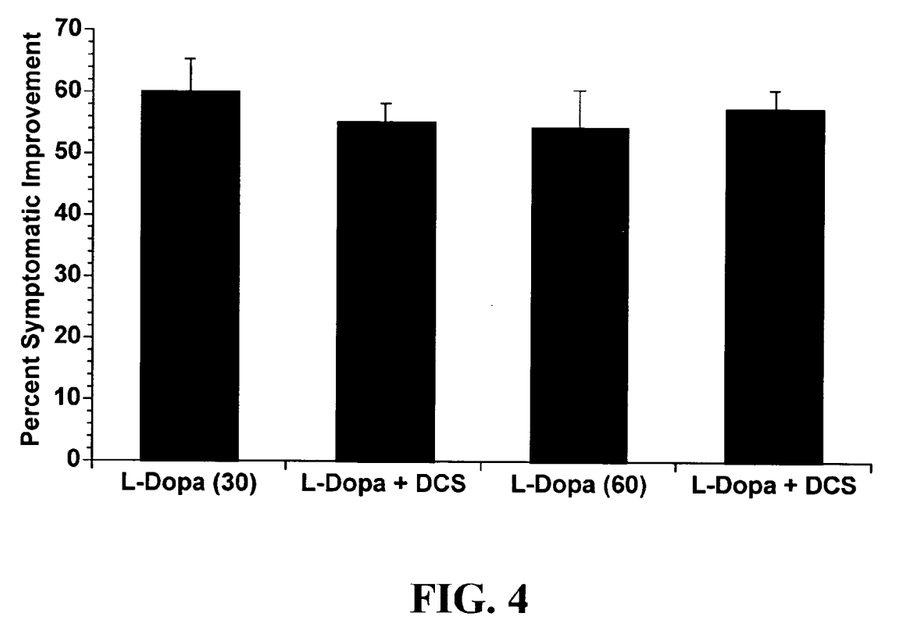
FIG. 4 is a histogram showing that administration of D-cycloserine ("DCS") with levodopa/benserazide ("L-Dopa") did not interfere with or reduce the symptomatic efficacy of L-Dopa when assessed thirty ("L-Dopa (30)") or sixty ("L-Dopa (60)") minutes after levodopa administration.

Addition of Partial Glycine Agonist D-Cycloserine to Levodopa Therapy Does Not Interfere with or Reduce the Anti-Parkinsonian Efficacy of Levodopa In two parkinsonian monkeys with an established therapeutic response to levodopa, peak-dose levodopa efficacy was assessed by raters blind to treatment condition. Eight mg/kg D-cycloserine was administered to the monkeys with 40 mg/kg levodopa plus 15 mg benserazide. As can be seen in FIG. 4, administration of the partial glycine agonist did not interfere with or reduce the therapeutic efficacy of levodopa (i.e., the ability of the levodopa to relieve symptoms of parkinsonism).

The data shown in the figures and discussed in the above Examples indicates that high doses of a partial glycine agonist are an effective anti-dyskinesia and anti-dystonia agent. Administration of high doses of a partial glycine agonist also counteracts the significant "wearing off" problem experienced by many patients that use levodopa, by extending the duration of effect of a levodopa dose. Furthermore, high doses of partial glycine agonist do not reduce or interfere with the therapeutic effect of levodopa.

All documents referred to herein are incorporated by reference. While the present invention has been described in connection with the preferred embodiments and the various figures, it is to be understood that other similar embodiments may be used or modifications and additions made to the described embodiments for performing the same function of the present invention without deviating therefrom. Therefore, the present invention should not be limited to any single embodiment, but rather should be construed in breadth and scope in accordance with the recitation of the appended claims.

What is claimed is:

1. A method for treating Parkinson's disease in a subject in need of such treatment, comprising administering levodopa and a partial glycine agonist selected from the group consisting of D-cycloserine and 1-aminocyclopropanecarboxylic acid to the subject, wherein the efficacy dose of partial glycine agonist is greater than 1 mg/kg and up to 12 mg/kg, and the of the levodopa is enhanced or the frequency and severity of levodopa-induced side effects in the subject is reduced.

2. The method of claim 1, wherein the partial glycine agonist is 1-aminocyclopropanecarboxylic acid.

3. The method of claim 1, wherein the partial glycine agonist is D-cycloserine.

4. The method of claim 1, further comprising administration of a peripheral dopa decarboxylase inhibitor.

5. The method of claim 4, wherein the peripheral dopa decarboxylase inhibitor is carbidopa or benserazide.

6. The method of claim 1, wherein the levodopa side effects are dyskinesias or dystonias.

7. The method of claim 1, wherein the dose of partial glycine antagonist is sufficient to deliver at least 8 mg of partial glycine agonist per kg body weight of the subject.

8. The method of claim 1, wherein the dose of partial glycine antagonist is sufficient to deliver 8 mg to 12 mg of partial glycine agonist per kg body weight of the subject.

9. The method of claim 1, wherein the levodopa and partial glycine agonist are administered simultaneously.

10. The method of claim 1, wherein the levodopa and partial glycine agonist are administered as a single-dose pharmaceutical composition.

11. The method of claim 1, wherein the levodopa or partial glycine agonist is administered enterally.

12. The method of claim 11, wherein the enteral administration is oral or rectal.

13. The method of claim 1, wherein the levodopa or partial glycine agonist is administered parenterally.

14. The method of claim 13, wherein the parenteral administration is selected from the group consisting of intravascular administration; subcutaneous injection, subcutaneous deposition intramuscular injection, intraperitoneal injection, transdermal, nasal and inhalational.

15. The method of claim 1, wherein the levodopa and partial glycine agonist are administered orally.

* * * * *